US00PP23440P3

(12) United States Plant Patent

Klemm et al.

(10) Patent No.: US PP23,440 P3

(45) Date of Patent: Feb. 26, 2013

(54) *GAURA* PLANT NAMED 'KLEGL10716'

(50) Latin Name: *Gaura lindheimeri*
Varietal Denomination: KLEGL10716

(75) Inventors: Nils Klemm, Stuttgart (DE); Martin Glawe, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 117 days.

(21) Appl. No.: 13/065,807

(22) Filed: Mar. 30, 2011

(65) Prior Publication Data

US 2012/0255088 P1 Oct. 4, 2012

(51) Int. Cl.
*A01H 5/00* (2006.01)

(52) U.S. Cl. ..... Plt./432

(58) Field of Classification Search ..... Plt./432
See application file for complete search history.

*Primary Examiner* — June Hwu

(74) *Attorney, Agent, or Firm* — Jondle & Associates, P.C.

(57) ABSTRACT

A new variety of *Gaura* plant named 'KLEGL10716', particularly characterized by an upright and bushy habit, good outdoor garden performance, and white flowers that last 3 to 4 days on the plant.

1 Drawing Sheet

Genus and species: *Gaura lindheimeri.*
Variety denomination: 'KLEGL10716'.

BACKGROUND OF THE NEW PLANT

The present invention comprises a new and distinct variety of *Gaura* plant, botanically known as *Gaura lindheimeri*, and hereinafter referred to by the variety name 'KLEGL10716'. The new *Gaura* variety was discovered as a seedling that was the result of a cross conducted in Stuttgart, Germany between the female parent *Gaura* plant 'GL 05 008' (unpatented) and the male parent *Gaura* plant 'GL 05 002' (unpatented). A single plant selection was subsequently chosen for further evaluation and asexual propagation.

The new *Gaura* variety 'KLEGL10716' was first propagated via vegetative cuttings in Stuttgart, Germany in April, 2009 and has been asexually reproduced repeatedly by vegetative cuttings in Stuttgart, Germany for approximately 3 to 4 generations. The new *Gaura* variety 'KLEGL10716' has been found to retain its distinctive characteristics through successive asexual propagations via vegetative cuttings.

Plant Breeder's Rights for this variety have not been applied for. 'KLEGL10716' has not been made publicly available or sold more than one year prior to the filing date of this application.

SUMMARY OF THE INVENTION

The following are the most outstanding and distinguishing characteristics of this new variety when grown under normal horticultural practices in a glass greenhouse in Stuttgart, Germany.

1. White flowers;
2. Good outdoor performance;
3. Upright, bushy habit; and
4. Flowers that last 3 to 4 days on the plant.

DESCRIPTION OF THE PHOTOGRAPH

The new *Gaura* variety 'KLEGL10716' is illustrated by the accompanying photograph which shows blooms, buds, and foliage of the plant. The colors shown are as true as can be reasonably obtained by conventional photographic procedures. The photograph is of a 12-week old plant taken in Stuttgart, Germany and grown from vegetative cuttings in a 12 centimeter plastic container in a glass greenhouse in Stuttgart, Germany under conditions which approximate those generally used in commercial practice.

DESCRIPTION OF THE NEW VARIETY

The following detailed descriptions set forth the distinctive characteristics of the new *Gaura* variety 'KLEGL10716'. The data which define these characteristics were collected from asexual reproductions carried out in Stuttgart, Germany from January through May of 2010. The plant history was taken on 3-month old plants that were grown in 12 centimeter containers in a glass greenhouse in Stuttgart, Germany. The plants were pinched once 10 days after planting. The color readings were determined under natural light. Color references are to The R.H.S. Colour Chart of The Royal Horticultural Society of London (R.H.S.), Fifth Edition (2007).

DETAILED BOTANICAL DESCRIPTION OF THE NEW PLANT

Classification:

*Family name.*—*Gaura.*
*Botanical name.*—*Gaura lindheimeri.*
*Common name.*—*Gaura* Belleza White.

Plant:

*Habit.*—Upright, bushy.
*Height.*—40 cm (when grown in a container).
*Spread.*—20 to 25 cm (when grown in a container).
*Outdoor or garden performance.*—Good, upright, 40 to 60 cm.

Propagation:

*Type.*—Cuttings.
*Blooming period.*—April to November.
*Time to initiate roots.*—Approximately 16 days.

*Time to produce a rooted young plant*.—Approximately 18 days.

*Root description*.—Fine, white.

Branches:

*Branching habit*.—Open, branching from base and stems.

*Number of lateral branches*.—6 to 8.

Stem:

*Diameter*.—4.0 to 5.0 cm.

*Length*.—20 to 35 cm.

*Shape*.—Cylindrical.

*Anthocyanin*.—Present.

*Anthocyanin color*.—RHS 185 B.

*Color of stem*.—RHS 138 A.

*Length of internode*.—0.5 to 0.7 cm.

*Pubescence*.—Slight.

Leaves:

*Arrangement*.—Alternate.

*Shape*.—Elongated oval.

*Attachment*.—Sessile.

*Margin*.—Entire.

*Apex*.—Acute.

*Base*.—Attenuate.

*Length*.—1.5 to 4.5 cm.

*Width*.—0.5 to 1.2 cm.

*Color*.—Immature leaves: Upper surface: RHS 138 A. Lower surface: RHS 138 B. Mature leaves: Upper surface: RHS N 137 A. Lower surface: RHS 137 C.

*Texture*.—Upper surface: Smooth. Lower surface: Smooth.

*Pubescence*.—Upper surface: Sparse. Lower surface: Absent.

*Venation pattern*.—Pinnate.

*Venation color*.—Upper surface: RHS 138 B. Lower surface: RHS 137 C to RHS 137 D. Anthocyanin color: RHS 137B.

Inflorescence:

*Blooming season*.—April to the end of October.

*Type*.—Spike.

*Shape*.—Explanate.

*Height or depth*.—8.0 cm.

*Width*.—4.0 cm.

Flowers:

*Average flower length*.—1.8 cm.

*Average flower width*.—0.8 cm.

*Peduncle*.—Length: 13.0 cm. Diameter: 2.0 mm. Strength: Small. Texture: Smooth. Angle: Upright. Color: RHS 138 D.

*Pedicel*.—Length: 8.0 mm. Diameter: 2.0 mm. Color: In the greenhouse until beginning of flowering: RHS 138D and RHS 70C. Outside: RHS 70A to RHS 70C. Surface texture: Smooth.

*Bud*.—Diameter: 2.0 mm. Length: 8.0 mm. Shape: Linear to narrow oval. Texture: Slightly pubescent. Color: RHS 150C.

*Sepals*.—Number: 2. Length: 14.0 mm. Width: 3.0 mm. Shape: Linear. Apex: Acute. Base: Alternate. Margin: Entire. Texture (both upper and lower surfaces): Smooth. Color: Upper surface: RHS 54C. Lower surface: RHS 150D.

*Petals*.—Number: 4. Shape: Ovate. Margin: Entire. Apex: Rounded. Base: Connate. Length: 15.0 mm. Width: 10.0 mm. Color: Upper surface: RHS NN 155 D. Lower surface: RHS NN 155 D. Texture (both upper and lower surfaces): Smooth.

*Number of flowers per inflorescence*.—5 to 12.

*Lastingness of flowers on the plant*.—3 to 4 days.

*Fragrance*.—None observed.

Reproductive organs:

*Stamens*.—Number per flower: 8. Length: 0.8 cm.

*Anthers*.—Shape: Ovate. Length: 3.0 mm. Diameter: 0.5 mm. Color: RHS 60C. Pollen quantity: Moderate.

*Filament color*.—RHS 158D.

*Pistils*.—Number: 1. Length: 0.15 cm. Shape: Four-lobed.

*Stigma color*.—RHS 150D.

*Style*.—Shape: Linear. Color: RHS 2D.

Fruit and seed set: None observed.

COMPARISON WITH PARENTAL AND COMMERCIAL VARIETIES

'KLEGL10716' differs from the female parent *Gaura* variety 'GL 05 008' (unpatented), in that 'KLEGL10716' has medium growth, medium to large sized flowers, and strong branching, while 'GL 05 008' has strong growth, large flowers, and medium branching.

'KLEGL10716' differs from the male parent *Gaura* variety 'GL 05 002' (unpatented), in that 'KLEGL10716' has medium growth, early flowering and medium to large sized flowers, while 'GL 05 002' has strong growth, late flowering and small sized flowers. In addition, 'KLEGL10716' has strong branching, while 'GL 05 002' has medium branching.

'KLEGL10716' differs from the commercial comparison variety 'Crimson Butterflies' (U.S. Plant Pat. No. 13,189), in that 'Crimson Butterflies' has crimson leaves, while 'KLEGL10716' has green leaves. In addition, 'Crimson Butterflies' has a very compact plant habit, while 'KLEGL10716' has an upright, bushy habit.

We claim:

1. A new and distinct variety of *Gaura* plant named 'KLEGL10716' as shown and described herein.

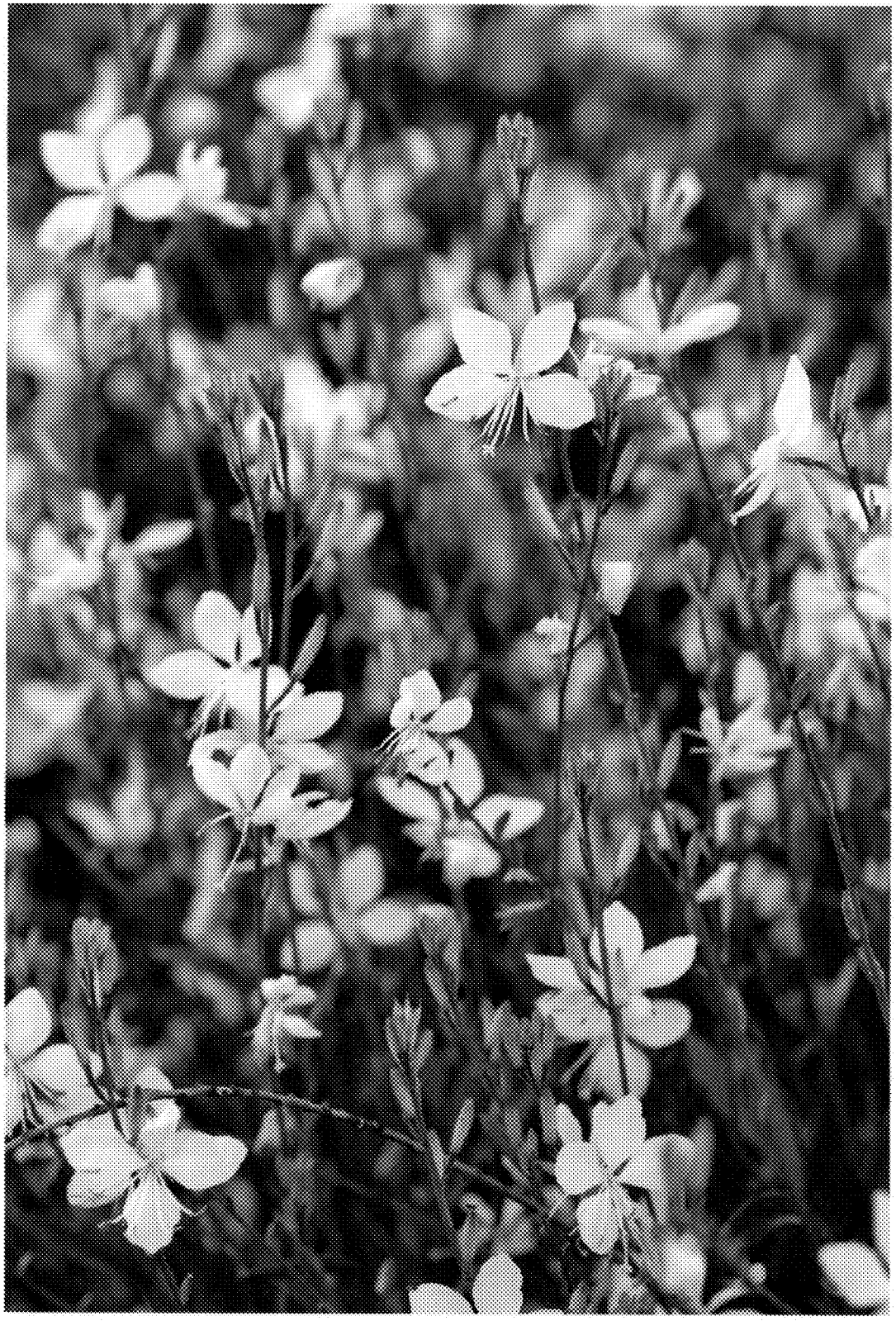

* * * * *